(12) United States Patent
Park et al.

(10) Patent No.: US 11,730,364 B2
(45) Date of Patent: Aug. 22, 2023

(54) APPARATUS AND METHODS FOR SUPPORTING READING OF FUNDUS IMAGE

(71) Applicant: XAIMED Co., Ltd., Seoul (KR)

(72) Inventors: Sang Min Park, Seoul (KR); Joo Young Chang, Seoul (KR); Choong Hee Lee, Seoul (KR); Il Hyung Shin, Jeju-si (KR)

(73) Assignee: XAIMED CO., LTD., Seoul (KR)

( * ) Notice: Subject to any disclaimer, the term of this patent is extended or adjusted under 35 U.S.C. 154(b) by 390 days.

(21) Appl. No.: 17/145,389

(22) Filed: Jan. 10, 2021

(65) Prior Publication Data

US 2021/0228073 A1   Jul. 29, 2021

(30) Foreign Application Priority Data

Jan. 29, 2020   (KR) .................. 10-2020-0010154

(51) Int. Cl.
| | |
|---|---|
| *A61B 3/12* | (2006.01) |
| *A61B 3/00* | (2006.01) |
| *G06T 7/00* | (2017.01) |
| *G06T 5/00* | (2006.01) |
| *G06T 3/40* | (2006.01) |

(Continued)

(52) U.S. Cl.
CPC ............. *A61B 3/12* (2013.01); *A61B 3/005* (2013.01); *A61B 3/0025* (2013.01); *G06N 20/00* (2019.01); *G06T 3/40* (2013.01); *G06T 5/002* (2013.01); *G06T 7/0012* (2013.01); *G06T 7/73* (2017.01); *G06V 10/454* (2022.01); *G06V 10/764* (2022.01); *G06V 10/82* (2022.01); *G16H 30/20* (2018.01); *G16H 50/20* (2018.01); *G06T 2207/30041* (2013.01); *G06V 2201/03* (2022.01)

(58) Field of Classification Search
CPC ........ G06T 7/73; G06T 7/0012; A61B 3/0016
See application file for complete search history.

(56) References Cited

U.S. PATENT DOCUMENTS

| | | | |
|---|---|---|---|
| 9,901,249 B2 * | 2/2018 | Muto ...................... A61B 3/12 |
| 10,052,016 B2 * | 8/2018 | Ehlers .................. G06V 40/197 |

(Continued)

FOREIGN PATENT DOCUMENTS

| | | | | |
|---|---|---|---|---|
| KR | 101848321 B1 | 4/2018 | | |
| WO | WO-2018116321 A2 * | 6/2018 | ............... G06T 7/20 |
| WO | WO-2019083129 A1 * | 5/2019 | ............... A61B 3/12 |

OTHER PUBLICATIONS

Machine translation of WO-2019083129-A1 (Year: 2019).*

*Primary Examiner* — John Villecco
*Assistant Examiner* — Courtney Joan Nelson
(74) *Attorney, Agent, or Firm* — Han's Law Office

(57) ABSTRACT

Provided are apparatuses, a non-transitory computer-readable medium or media, and methods for supporting reading of a fundus image of a subject. In certain aspects, disclosed a method including the steps of: extracting a first feature information from a first fundus image of the subject based on a machine learning model; generating a second fundus image having a second feature information by mapping an adversarial factor to the first fundus image so that the first feature information is changed; and displaying the first fundus image having the first feature information and the second fundus image having the second feature information on a display device.

**17 Claims, 11 Drawing Sheets
(7 of 11 Drawing Sheet(s) Filed in Color)**

Obtaining a first fundus image of a subject form a camera and Extracting a first feature information from a first fundus image — S910

Generating a second fundus image having a second feature information by mapping an adversarial factor to the first image so that the first feature information is changed — S920

Displaying the first fundus image having the first feature information and the second fundus image having the second feature information on a display device — S930

(51) Int. Cl.
*G06T 7/73* (2017.01)
*G06N 20/00* (2019.01)
*G16H 30/20* (2018.01)
*G16H 50/20* (2018.01)
*G06V 10/764* (2022.01)
*G06V 10/82* (2022.01)
*G06V 10/44* (2022.01)

(56) References Cited

U.S. PATENT DOCUMENTS

| | | | | |
|---|---|---|---|---|
| 10,111,582 B2* | 10/2018 | Nakagawa | ............ | G06T 7/0012 |
| 2016/0292856 A1* | 10/2016 | Niemeijer | ............... | G06V 10/82 |
| 2019/0108917 A1* | 4/2019 | Suehling | ................ | G16H 30/40 |

* cited by examiner

APPARATUS AND METHODS FOR SUPPORTING READING OF FUNDUS IMAGE

TECHNICAL FIELD

The present disclosure relates to diagnosing disease of biometric images, more particularly, to an apparatus and method for supporting reading of fundus images using a machine learning model.

DESCRIPTION OF THE RELATED ART

With development of artificial intelligence learning models, many machine learning models are being used to read medical images. For example, the machine learning models such as Convolutional Neural Networks (CNN), Deep Neural Networks (DNN), Recurrent Neural Networks (RNN), and Deep Belief Networks (DBN) are being applied to detect, classify, and characterize the medical images.

In particular, in a fundus image of the medical images, the machine learning models are currently being used to support an image reading, an image finding, an image diagnosis in order to predict a disease of a patient. More specifically, a method of supporting the image reading, the image finding, the image diagnosis of the fundus image is to obtain the fundus image from the patient, extract feature from the fundus image based on the machined learning models, provide the feature to a practitioner, and predict the patient's disease based on it. In this case, the feature includes various information for the fundus image.

However, even if the feature of the fundus image is extracted based on the machine learning model, if the learning information input to the machine learning model is inadequate or insufficient for various factors such as a lack of learning data input to the machine learning mode, differences in environments of fundus imaging (e.g., a health check-up center, a private ophthalmology clinic, a general hospital, etc.), a difference of learning data (e.g., only a fundus image of a normal person, only a fundus image of an abnormal person), a difference of an imaging apparatuses, an entity such as a medical practitioner can receive incorrect information from the machined learning model. For example, differences in learning information are the lack of learning data input to the learning model, differences in imaging environments (e.g., health examination centers, private ophthalmology hospitals, general ophthalmology hospitals), and groups (e.g., only normal people, only abnormalities). It may be a difference between a person, a normal person and an abnormal person), a difference between an imaging device, and the like. These various factors can lead to erroneous prediction of the patient's disease.

Thus, even though the learning information is poor, there is a need for systems and methods that can do the more accurate prediction of the patient's disease using the learning information image and can explain why such the patient's disease was predicted.

SUMMARY OF THE DISCLOSURE

In one aspect of the present disclosure, an apparatus for supporting reading of a fundus image of a subject includes a processor and a memory including one or more sequences of instructions which, when executed by the processor, causes steps to be performed includes: extracting a first feature information from a first fundus image of the subject based on a machine learning model; generating a second fundus image having a second feature information by mapping an adversarial factor to the first fundus image so that the first feature information is changed; and displaying the first fundus image having the first feature information and the second fundus image having the second feature information on a display device.

Desirably, the steps further may include generating images in which a specific area of each of the first fundus image and the second fundus image is enlarged; and displaying the images on the display device.

Desirably, the steps further may include generating a third fundus image in which an adversarial noise is visualized, by filtering the second fundus image mapped by the adversarial factor therein; and displaying the third fundus image on the display device.

Desirably, the steps further may include generating a pre-first fundus image by pre-processing the first fundus image so that a specific area of the first fundus image is enlarged or partially partitioned.

In another aspect of the present disclosure, a non-transitory computer-readable medium or media include one or more sequences of instructions which, when executed by a processor, causes steps for supporting reading of a fundus image of a subject, includes extracting a first feature information from a first fundus image of the subject based on a machine learning model; generating a second fundus image having a second feature information by mapping an adversarial factor to the first fundus image so that the first feature information is changed; and displaying the first fundus image having the first feature information and the second fundus image having the second feature information on a display device.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

References will be made to embodiments of the disclosure, examples of which may be illustrated in the accompanying figures. These figures are intended to be illustrative, not limiting. Although the disclosure is generally described in the context of these embodiments, it should be understood that it is not intended to limit the scope of the disclosure to these particular embodiments.

DETAILED DESCRIPTION OF PREFERRED EMBODIMENTS

Figure 1:
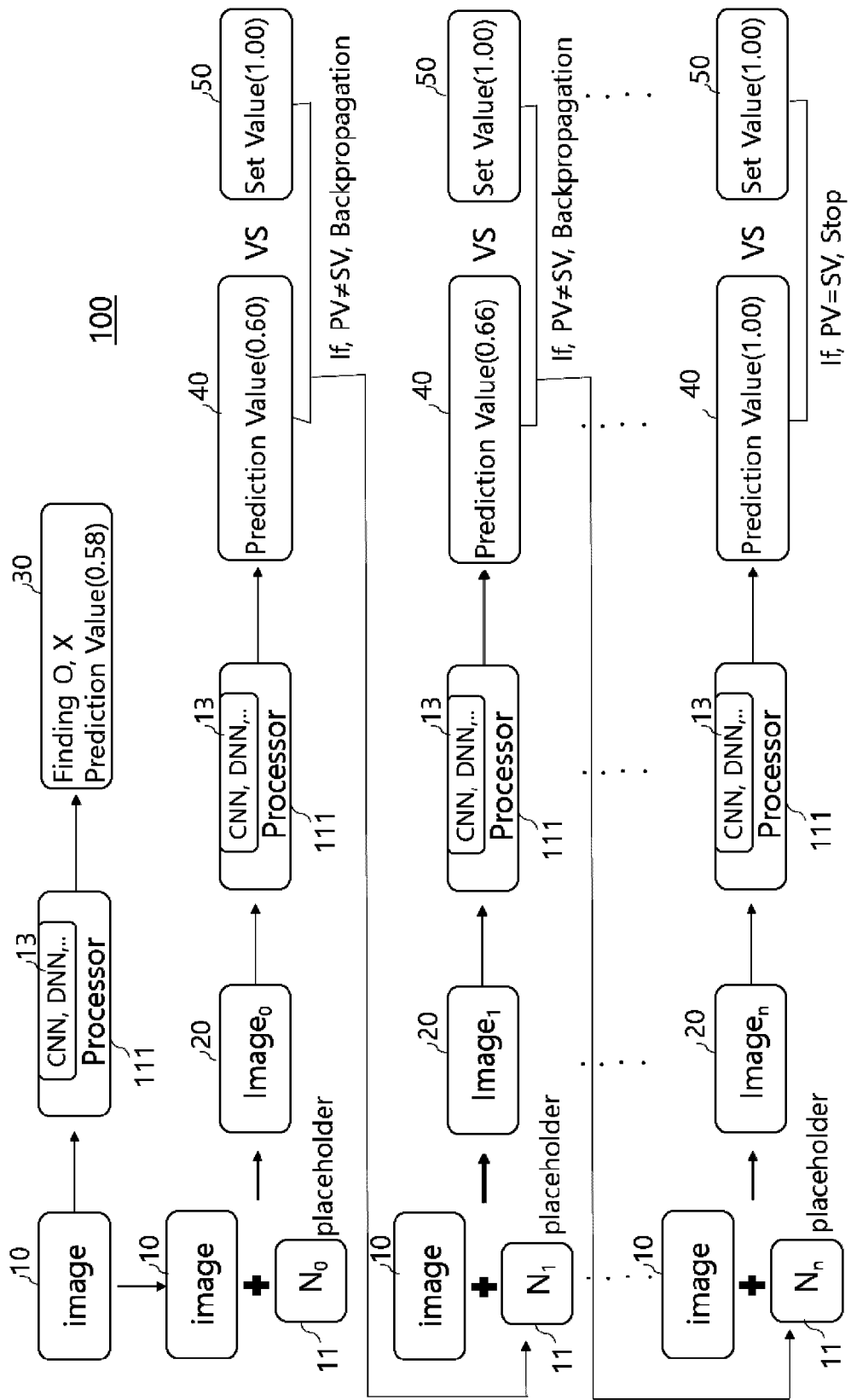
FIG. 1 shows a flowchart of an illustrative process for generating a feature information of a fundus image according to embodiments of the present disclosure.

The patent or application file contains at least one drawing executed in color. Copies of this patent or patent application publication with color drawings will be provided by the Office upon request and payment of the necessary fee.

In the following description, for purposes of explanation, specific details are set forth in order to provide an understanding of the disclosure. It will be apparent, however, to one skilled in the art that the disclosure can be practiced without these details. Furthermore, one skilled in the art will recognize that embodiments of the present disclosure, described below, may be implemented in a variety of ways, such as a process, an apparatus, a system, a device, or a method on a tangible computer-readable medium.

Components shown in diagrams are illustrative of exemplary embodiments of the disclosure and are meant to avoid obscuring the disclosure. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof.

It shall also be noted that the terms "coupled," "connected," "linked," or "communicatively coupled" shall be understood to include direct connections, indirect connections through one or more intermediary devices, and wireless connections.

Furthermore, one skilled in the art shall recognize: (1) that certain steps may optionally be performed; (2) that steps may not be limited to the specific order set forth herein; and (3) that certain steps may be performed in different orders, including being done contemporaneously.

Reference in the specification to "one embodiment," "preferred embodiment," "an embodiment," or "embodiments" means that a particular feature, structure, characteristic, or function described in connection with the embodiment is included in at least one embodiment of the disclosure and may be in more than one embodiment. The appearances of the phrases "in one embodiment," "in an embodiment," or "in embodiments" in various places in the specification are not necessarily all referring to the same embodiment or embodiments.

In the following description, it shall also be noted that the terms "learning" shall be understood not to intend mental action such as human educational activity because of referring to performing machine learning by a processing module such as a processor, a CPU, an application processor, micro-controller, so on.

An "image" is defined as a reproduction or imitation of the form of a person or thing, or specific characteristics thereof, in digital form. An image can be, but is not limited to, a JPEG image, a PNG image, a GIF image, a TIFF image, or any other digital image format known in the art. "Image" is used interchangeably with "photograph".

A "feature(s)" is defined as a group of one or more descriptive characteristics of subjects that can discriminate for disease. A feature can be a numeric attribute.

The terms "comprise/include" used throughout the description and the claims and modifications thereof are not intended to exclude other technical features, additions, components, or operations.

Unless the context clearly indicates otherwise, the singular forms "a," "an," and "the" are intended to include the plural forms as well. Also, when description related to a known configuration or function is deemed to render the present disclosure ambiguous, the corresponding description is omitted.

The embodiments described herein relate generally to diagnostic medical images. Although any type of medical image can be used, these embodiments will be illustrated in conjunction with fundus images. However, the disclosed methods, systems, apparatuses and devices can also be used with medical images of other ocular structures, or any other biological tissues image of which can support the diagnosis of a disease condition. Furthermore, the methods disclose herein can be used with a variety of imaging modalities including but not limited to: computed tomography (CT), magnetic resonance imaging (MRI), computed radiography, magnetic resonance, angioscopy, optical coherence tomography, color flow Doppler, cystoscopy, diaphanography, echocardiography, fluoresosin angiography, laparoscopy, magnetic resonance angiography, positron emission tomography, single photon emission computed tomography, x-ray angiography, nuclear medicine, biomagnetic imaging, culposcopy, duplex Doppler, digital microscopy, endoscopy, fundoscopy, laser, surface scan, magnetic resonance spectroscopy, radio graphic imaging, thermography, and radio fluroscopy.

FIG. 1 shows a flowchart of an illustrative process for generating a feature information of a fundus image by an apparatus 100 according to embodiments of the present disclosure. As depicted, in embodiments, a processor 111 may extract a first feature information 30 from a first fundus image 10 that is photographed by imaging means such as a camera, using a machine learning model 13 (e.g., CNN, DNN, etc.). The extracted first feature information 30 may be stored in a memory unit 113 or a storage device 115 described below. In embodiments, the machine learning model 13 may be installed into a processor 111 and executed by the processor 111. The machine learning model 13 may be installed into a computer-readable medium or media (not shown in FIG. 1) and executed by the computer-readable medium or media. In alternative embodiments, the machine learning model 13 may be installed into the memory unit 113 or the storage device 115 and executed by the processor 111.

In addition, the processor 111 may store clinical information of a subject (e.g., a patient) in the memory unit 113 or the storage device 115 in advance. In embodiments, the processor 111 may extract the first feature information of the first fundus image 10 based on the machine learning model 13 by using the clinical information of the subject stored in the memory unit 113 or the storage device 115. In embodiments, the clinical information may be, but is not limited to, the age, sex, medical history, questionnaire information, test measurement values, exercise habits, eating habits, family history related to the medical history, alcohol consumption, smoking status. In embodiments, the questionnaire information may include neuromedical questionnaire that a practitioner (e.g., a medical doctor) can perform on the subject or may mean ideal findings currently observed to the subject, unlike medical history thereof. In embodiments, the test measurement values may include an intraocular pressure, a blood pressure, a blood sugar level, and the like.

In embodiments, the first feature information 30 may be various information that it can support an entity (e.g., a practitioner or a computing device) reading an fundus image such as predicting or diagnosing disease. For instance, when predicting or diagnosing glaucoma in the fundus image of the subject, the first feature information may include at least one of various information such as the increased C/D ratio (Cup-to-Disk ratio) information, thickness change information for Disc Rim Thinning, contrast information for Retinal Nerve Fiber Layer Defect, or location information of Retinal Hemorrhage included in the fundus image. For another instance, when predicting or diagnosing diabetic retinopathy in the fundus image of the subject, the first feature information may include at least one of location information on Drusen, information on Retinal Pigment Epithelium Change, information on Chorioretinal Scar/Atrophy, information on Peripapillary Atrophy, information on Hard Exudate, information on Cotton-Wool Patch, information on Hemorrhage, information on Vascular Abnormality, information on Laser Scar, information on Subretinal Fluid, information on Myelinated Nerve Fiber, and information on Epiretinal Membrane included in the fundus image. In addition, the first feature information may include at least one of optic nerve vascular information that provides information on major organs of the eyeball, binocular classification information indicating whether the fundus image is an image of the left eye or the right eye, location information indicating a location of at least one of the macular and optic disk, and partitioning information indicating a segment of the fundus image and the like in the fundus image.

In this case, in embodiments, on the results performed by the processor 111, the apparatus 100 may appear the finding (Finding O, X) indicating the presence or absence of a disease in the fundus image on the basis of the first feature information, or a prediction value indicating the presence or absence of the finding on a display device 130, 330 describe below. In embodiments, the prediction value may be expressed as a percentage or a number between 0 and 1, an explanation of presence or absence of the finding and the prediction value will be described in more detail below.

Meanwhile, in embodiments, the processor 111 may generate a second fundus image 20, that is another image artificially made similar to the first fundus image 10 using a GAN (Generative Adversarial Networks) learning model.

In preferred embodiments, the processor 111 may generate a second fundus image 20 that is made using a photographed original image (i.e., the first fundus image 10). The photographed original image can more accurately reflect its own feature information rather than another image artificially made similar to the first fundus image 10 using a GAN (Generative Adversarial Networks) learning model. Therefore, the feature information of the second fundus image 20 that is made using a photographed original image may have better reliability. More specifically, the processor 111 may map an adversarial factor 11 into the first fundus image 10. By doing so, the first feature information 30 of the first fundus image 10 is changed so that it may generate the second fundus image 20 including a second feature information 40. In embodiments, the generated second fundus image 20 including the second feature information 40 may be stored in the memory unit 113 or the storage device 115 described below.

In embodiments, the adversarial factor 11 may be adversarial noise ($N_0, \ldots, N_n$) that is attacked to the first fundus image 10. For example, the adversarial noise may include at least one of a value that adjusts the gradation level of the R, G, and B pixels representing the first fundus image 10, a value that adjusts the color of the R, G, and B pixels of the first fundus image 10, a value that locally adjusts the contrast ratio in the first fundus image 10. It should be noted that the adversarial factor 11 may include any factor that can change the first feature information of the first fundus image 10.

In embodiments, the second fundus image 20 including the second feature information 40 may be generated by mapping the adversarial factor 11 to the first fundus image 10 once. In alternative embodiments, the second fundus image 20 including the second feature information 40 may be generated by repeatedly mapping the adversarial factor 11 to the first fundus image 10 so that the prediction value for the second feature information 40 obtained based on the machine learning model 13 converges to a set value 50. For instance, if the set value is 1 and the prediction value of the first fundus image 10 obtained based on the machine learning model 13 is 0.58, the adversarial factor 11 is mapped to the first fundus image 10 by the processor 111, thereby being generated by the second fundus image 20, and then, the first fundus image 10 may be repeatedly mapped by the adversarial factor 11 so that the prediction values (0.60, 0.66, 0.68, . . . ) of the generated second fundus image 20 obtained based on the machine learning model 13 converges to the set value 1. For another instance, if the set value is 0 and the prediction value of the first fundus image obtained based on the machine learning model 13 is 0.58, the first fundus image 10 is mapped by the adversarial factor 11, thereby being generated by the second fundus image 20, and then, the first fundus image 10 may be repeatedly mapped by the adversarial factor 11 so that the prediction values (0.56, 0.54, 0.52, . . . ) of the generated second fundus image 20 obtained based on the machine learning model 13 converges to the set value 0. Thus, the number of second fundus images 20 may be determined according to the number of set values.

If the set value is 1, it may mean that the generated fundus image (the second fundus image 20) is a fundus image that is close to an abnormal fundus image in which any disease can be predicted or diagnosed thereon. In such case, it may mean that there is the finding. if the set value is 0, it may mean that the generated fundus image (the second fundus image 20) is a fundus image that is close to a normal fundus image in which any disease cannot be predicted or diagnosed thereon. In such case, it may mean that there is no the finding.

In embodiments, the first fundus image 10 having the first feature information 30 obtained based on the machine learning model 13 and the second fundus image 20 having the second feature information 40 obtained by mapping the adversarial factor 11 may be provided to at least one of a practitioner (e.g., a medical doctor) through a transmission module such as a display adapter 118 or a network adapter 119, one and more remote computing devices 200, 300, 400 that is linked to the computing device 110 through an Internet network, and the other device that can use the fundus image 10 and the second fundus image 20, described below.

In embodiments, since the second fundus image 20 with the second feature information 40 is a fundus image close to the normal or abnormal fundus image, when the entity (e.g., the practitioner, the remote computing device) reads the first fundus image 10, the apparatus 100 may allow the entity to read the first fundus image 10 by comparing it with the second fundus image 20, so that the entity can easily and accurately read the first fundus image 10. In addition, since the processor 111 may generate a comparison image (i.e., the second fundus image 20) for the first fundus image 10, and compare the comparison image with the first fundus image 10, it is possible to convincingly explain the reason why such a reading result is obtained for the first fundus image 10. Accordingly, the reliability of the reading of the first fundus image 10 having the first feature information 30 can be improved.

In addition, in embodiments, the apparatus 100 may display a difference between the first feature information 30 of the first fundus image 10 and the second feature information 40 of the second fundus image 20 on the display device 130 described below and may provide the difference to the entity.

Figure 2:
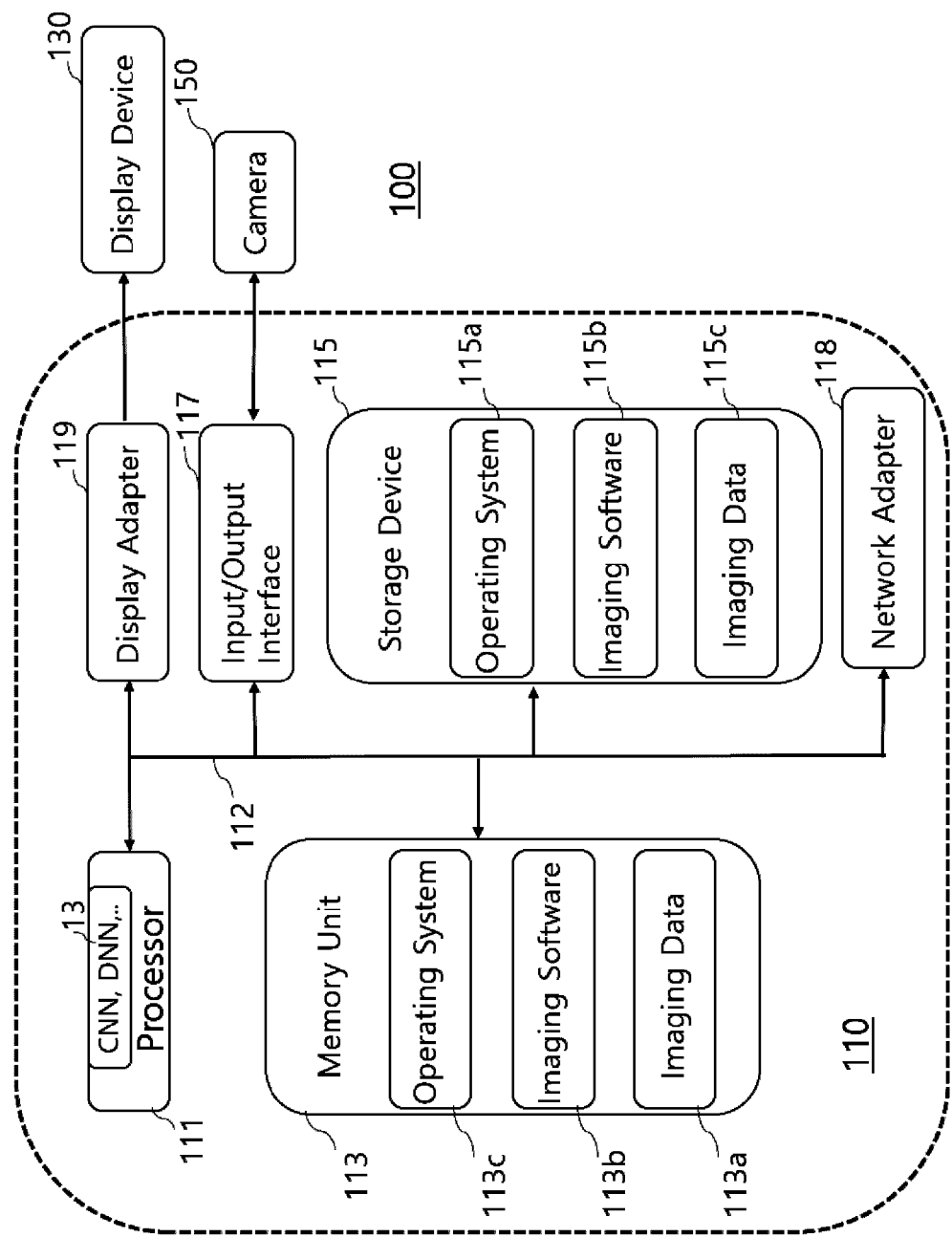
FIG. 2 shows a schematic diagram of an illustrative apparatus for supporting reading of a fundus image according to embodiments of the present disclosure.

FIG. 2 is a schematic diagram of an illustrative apparatus 100 for supporting reading of a fundus image according to embodiments of the present disclosure.

As depicted, the apparatus 100 may include a computing device 110, a display device 130 and a camera 150. In embodiments, the computing device 110 may include, but is not limited thereto, one or more processor 111, a memory unit 113, a storage device 115, an input/output interface 117, a network adapter 118, a display adapter 119, and a system bus 112 connecting various system components to the memory unit 113. In embodiments, the apparatus 100 may further include communication mechanisms as well as the system bus 112 for transferring information. In embodiments, the communication mechanisms or the system bus 112 may interconnect the processor 111, a computer-readable medium, a short range communication module (e.g., a Bluetooth, a NFC), the network adapter 118 including a network interface or mobile communication module, the display device 130 (e.g., a CRT, a LCD, etc.), an input device (e.g., a keyboard, a keypad, a virtual keyboard, a mouse, a trackball, a stylus, a touch sensing means, etc.) and/or subsystems. In embodiments, the camera 150 may include an image sensor (not shown) that captures an image of an subject and photoelectrically converts the image into an image signal, and may photograph a fundus image of the subject using the image sensor. The photographed fundus image may be stored in the memory unit 113 or the storage device 115, or may be provided to the processor 111 through the input/output interface 117 and processed based on the machine learning model 13.

In embodiments, the processor 111 is, but is not limited to, a processing module, a Computer Processing Unit (CPU), an Application Processor (AP), a microcontroller, a digital signal processor. In embodiments, the processor 111 may include an image filter such as a high pass filter or a low pass filter to filter a specific factor in a fundus image. In addition, in embodiments, the processor 111 may communicate with a hardware controller such as the display adapter 119 to display a user interface on the display device 130. In embodiments, the processor 111 may access the memory unit 113 and execute commands stored in the memory unit 113 or one or more sequences of instructions to control the operation of the apparatus 100. The commands or sequences of instructions may be read in the memory unit 113 from computer-readable medium or media such as a static storage or a disk drive, but is not limited thereto. In alternative embodiments, a hard-wired circuitry which is equipped with a hardware in combination with software commands may be used. The hard-wired circuitry can replace the soft commands. The instructions may be an arbitrary medium for providing the commands to the processor 111 and may be loaded into the memory unit 113.

In embodiments, the system bus 112 may represent one or more of several possible types of bus structures, including a memory bus or memory controller, a peripheral bus, an accelerated graphics port, and a processor or local bus using any of a variety of bus architectures. For instance, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. In embodiments, the system bus 112, and all buses specified in this description can also be implemented over a wired or wireless network connection.

A transmission media including wires of the system bus 112 may include at least one of coaxial cables, copper wires, and optical fibers. For instance, the transmission media may take a form of sound waves or light waves generated during radio wave communication or infrared data communication.

In embodiments, the apparatus 100 may transmit or receive the commands including messages, data, and one or more programs, i.e., a program code, through a network link or the network adapter 118. In embodiments, the network adapter 118 may include a separate or integrated antenna for enabling transmission and reception through the network link. The network adapter 118 may access a network and communicate with a remote computing devices 200, 300, 400 in FIG. 3.

In embodiments, the network may be, but is not limited to, at least one of LAN, WLAN, PSTN, and cellular phone networks. The network adapter 118 may include at least one of a network interface and a mobile communication module for accessing the network. In embodiments, the mobile communication module may be accessed to a mobile communication network for each generation such as 2G to 5G mobile communication network.

In embodiments, on receiving a program code, the program code may be executed by the processor 111 and may be stored in a disk drive of the memory unit 113 or in a non-volatile memory of a different type from the disk drive for executing the program code.

In embodiments, the computing device 110 may include a variety of computer-readable medium or media. The computer-readable medium or media may be any available medium or media that are accessible by the computing device 100. For example, the computer-readable medium or media may include, but is not limited to, both volatile and non-volatile media, removable or non-removable media.

In embodiments, the memory unit 113 may store a driver, an application program, data, and a database for operating the apparatus 100 therein. In addition, the memory unit 113 may include a computer-readable medium in a form of a volatile memory such as a random access memory (RAM), a non-volatile memory such as a read only memory (ROM), and a flash memory. For instance, it may be, but is not limited to, a hard disk drive, a solid state drive, an optical disk drive.

In embodiments, each of the memory unit 113 and the storage device 115 may be program modules such as the imaging software 113b, 115b and the operating systems 113c, 115c that can be immediately accessed so that a data such as the imaging data 113a, 115a is operated by the processor 111.

In embodiments, the machine learning model 13 may be installed into at least one of the processor 111, the memory unit 113 and the storage device 115. The machine learning model 13 may be, but is not limited to, at least one of a deep neural network (DNN), a convolutional neural network (CNN) and a recurrent neural network (RNN), which are one of the machine learning algorithms.

Figure 3:
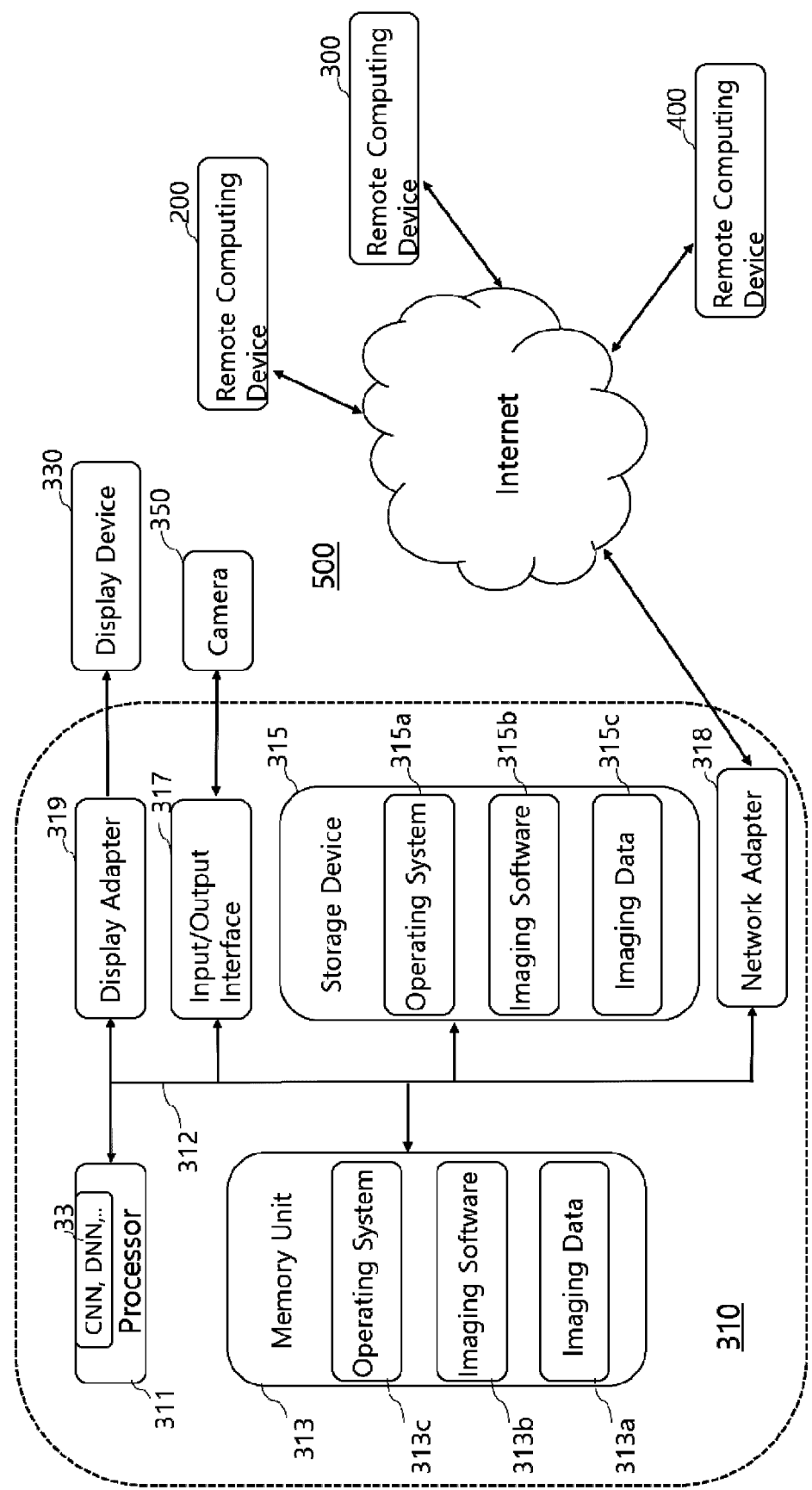
FIG. 3 shows a schematic diagram of an illustrative system for supporting reading of a fundus image according to embodiments of the present disclosure.

FIG. 3 is a schematic diagram of an illustrative system 500 for supporting reading of a fundus image according to embodiments of the present disclosure.

As depicted, the system 500 may include a computing device 310 and one and more remote computing devices 200, 300, 400. In embodiments, the computing device 310 and the remote computing devices 200, 300, 400 may be connected to each other through a network. The components 310, 311, 312, 313, 315, 317, 318, 319, 330 of the system 500 are similar to their counterparts in FIG. 2. In embodiments, each of remote computing devices 200, 300, 400 may be similar to the apparatus 100 in FIG. 2. For instance, each of remote computing devices 200, 300, 400 may include each of the subsystems, including the processor 311, the memory unit 313, an operating system 313c, 315a, an imaging software 313b, 315b, an imaging data 313a, 315c, a network adapter 318, a storage device 315, an input/output interface 317 and a display adapter 319. Each of remote computing devices 200, 300, 400 may further include a display device 330 and a camera 350. In embodiments, the system bus 312 may connect the subsystems to each other.

In embodiments, the computing device 310 and the remote computing devices 200, 300, 400 may be configured to perform one or more of the methods, functions, and/or operations presented herein. Computing devices that implement at least one or more of the methods, functions, and/or operations described herein may comprise an application or applications operating on at least one computing device. The computing device may comprise one or more computers and one or more databases. The computing device may be a single device, a distributed device, a cloud-based computer, or a combination thereof.

It shall be noted that the present disclosure may be implemented in any instruction-execution/computing device or system capable of processing data, including, without limitation laptop computers, desktop computers, and servers. The present invention may also be implemented into other computing devices and systems. Furthermore, aspects of the present invention may be implemented in a wide variety of ways including software (including firmware), hardware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 4:
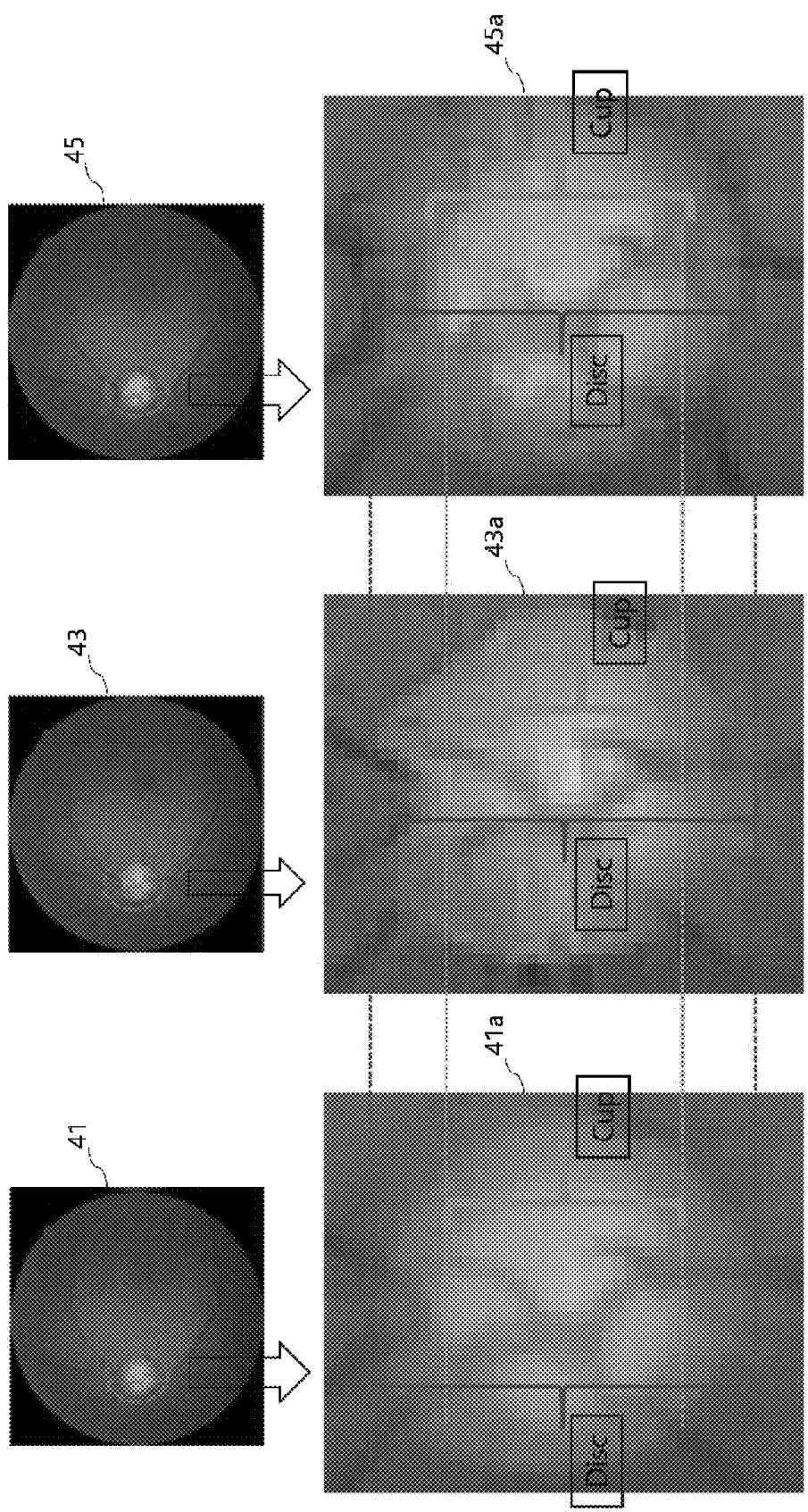
FIG. 4 is a view showing fundus images including a C/D ratio information acquired by an apparatus according to embodiments of the present disclosure.

FIG. 4 is a view showing fundus images including a C/D ratio information acquired by an apparatus 100 according to embodiments of the present disclosure. A value of the C/D ratio is defined as the value of the maximum distance of an area corresponding to a cup in the fundus image divided by the maximum distance of an area corresponding to a disc in a fundus image. Typically, the value of the C/D ratio may be a measure of predicting a disease such as glaucoma in the fundus image.

As depicted, a first fundus image 41 is obtained from the subject based on the machine learning model 13 of the apparatus 100 in FIG. 1, and an enlarged first image 41a is obtained by enlarging a cup and disc area in the first fundus image 41. A second fundus image 43 is obtained by mapping a negative adversarial factor to the cup and disc area of the first fundus image 41, the negative adversarial factor means an adversarial factor to make the prediction value converge to the set value 0 as mapping method by the processor 111 in described conjunction with FIG. 1. That is, the second fundus image 43 is an image with the C/D ratio in the normal range that cannot diagnose any disease based on the machine learning model, and an enlarged second image 43a is obtained by enlarging the cup and disc area in the second fundus image 43. A third fundus image 45 is obtained by mapping a positive adversarial factor to the cup and disc area of the first fundus image 41, the positive adversarial factor means an adversarial factor to make the prediction value converge to the set value 1 as mapping method by the processor 111 described in conjunction with FIG. 1. Namely, the third fundus image 45 is an image with the C/D ratio in the abnormal range that can diagnose any disease based on the machine learning model, and an enlarged third image 45a is obtained by enlarging the cup and disc area in the third fundus image 45. The enlarged first, second, third images 41a, 43a, 45a may be generated by the processor 111 processing each of the first, second, third fundus images 41, 43, 45. In this case, the first feature information of the first fundus image 41 shows the value of the C/D ratio, and the second feature information of the second fundus image 43 and the third feature information of the third fundus image 45 show the values of the C/D ratio changed by mapping the adversarial factor to the first fundus image 41. The method of mapping the adversarial factor may be similar to mapping described in FIG. 1.

More specifically, the first fundus image 41 obtained based on the machine learning model 13 is a fundus image that can show the findings (a practitioner's opinion) in which it appears any disease such as glaucoma. However, on reading the first fundus image 41, the accuracy or reliability of such findings on the first fundus image 41 may be poor. In embodiments, the processor 111 may generate the second fundus image 43 so that the value of the C/D ratio is close to the normal range of the fundus image, or the third fundus image 45 so that the value of the C/D ratio is close to the abnormal range of the fundus image. The second and third fundus images 43, 45 may be displayed on the display device 130 so that the entity can compare the first fundus image 41 with the second and third fundus images 43, 45. In alternative embodiments, the enlarged first, second, third image 41a, 43a, 45a generated by the processor 111 may be displayed on the display device 130 so that the entity can compare the enlarged first image 41a with the enlarged second and third images 43a, 45a. Since the apparatus 100 can allow the entity to compare the first fundus image with the second fundus image or the third fundus image when reading the fundus image, the reliability and accuracy of a reading (e.g., a finding, a prediction, a diagnosis) on the first fundus image by the apparatus 100 can be improved. Thus, the apparatus 100 can allow the entity to explain the reason why such the reading was obtained.

Figure 5:
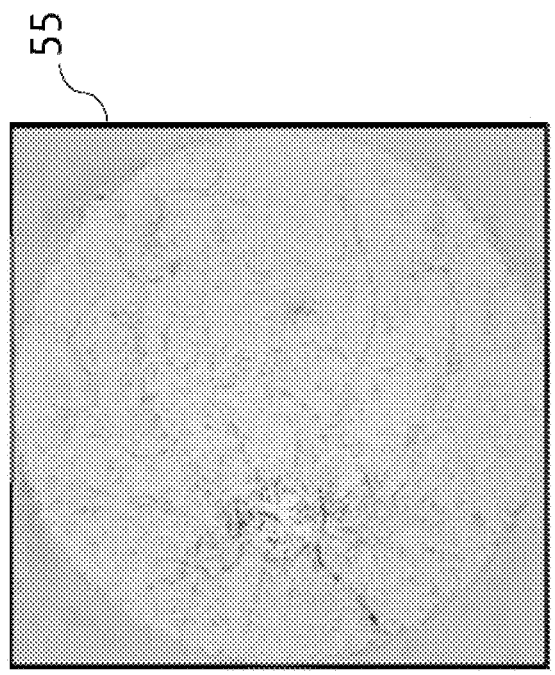
FIG. 5 is a view showing images obtained by filtering fundus images in FIG. 4 by an apparatus according to embodiments of the present disclosure.
Figure 5:
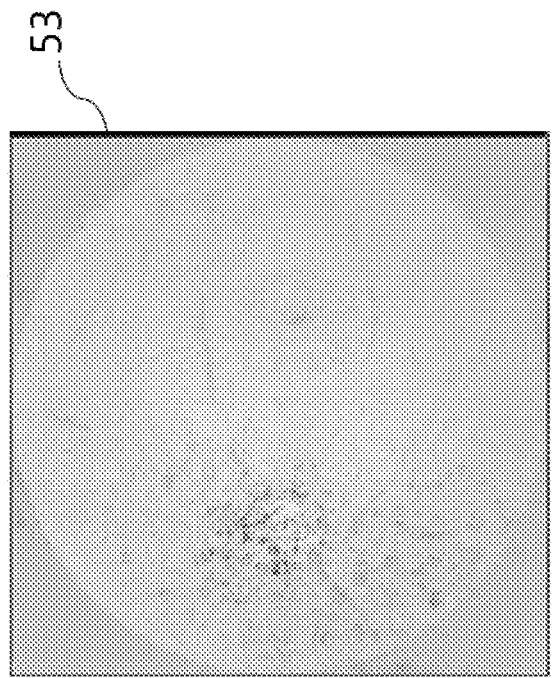

FIG. 5 is a view showing images obtained by filtering a second fundus image 43 and a third fundus image 45 in FIG. 4 using the processor 111 of the apparatus 100 according to embodiments of the present disclosure. As depicted, in embodiments, a first image 53 and second image 55 correspond with the second fundus image 43 and the third fundus image 45 in FIG. 4, respectively. The first image 53 and second image 55 are images visualizing the adversarial noise mapped to each of the second fundus image 43 and the third fundus image 45. The visualized images 53, 55 may be generated by filtering each of the second fundus image 43 and the third fundus image 45 having the adversarial noise using an image filter such as a high pass filter. The image filter may be executed by the processor 111 accordingly to the present disclosure. The visualized images 53, 55 may be provided to the entity so that the entity can compare the visualized images 53, 55 to each other.

It is shown that the adversarial noise such as a dot is mapped around a disc area where the C/D ratio information can be found in the fundus image. More specifically, the first image 53 shows that the adversarial noise is more intensively mapped to the disc area, as an image with the value of the C/D ratio in the normal range. The second image 55 shows that the adversarial noise is mapped not only to the disc area but also to the entire area of the fundus image, as an image with the value of the C/D ratio in the abnormal range.

Thus, the apparatus 100 may visualize the adversarial noise of the fundus image so that the entity knows the feature information in which the C/D ratio is changing at a certain position in the fundus image. Therefore, the apparatus 100 may allow the entity to read the fundus image with more the accuracy and reliability.

Figure 6:
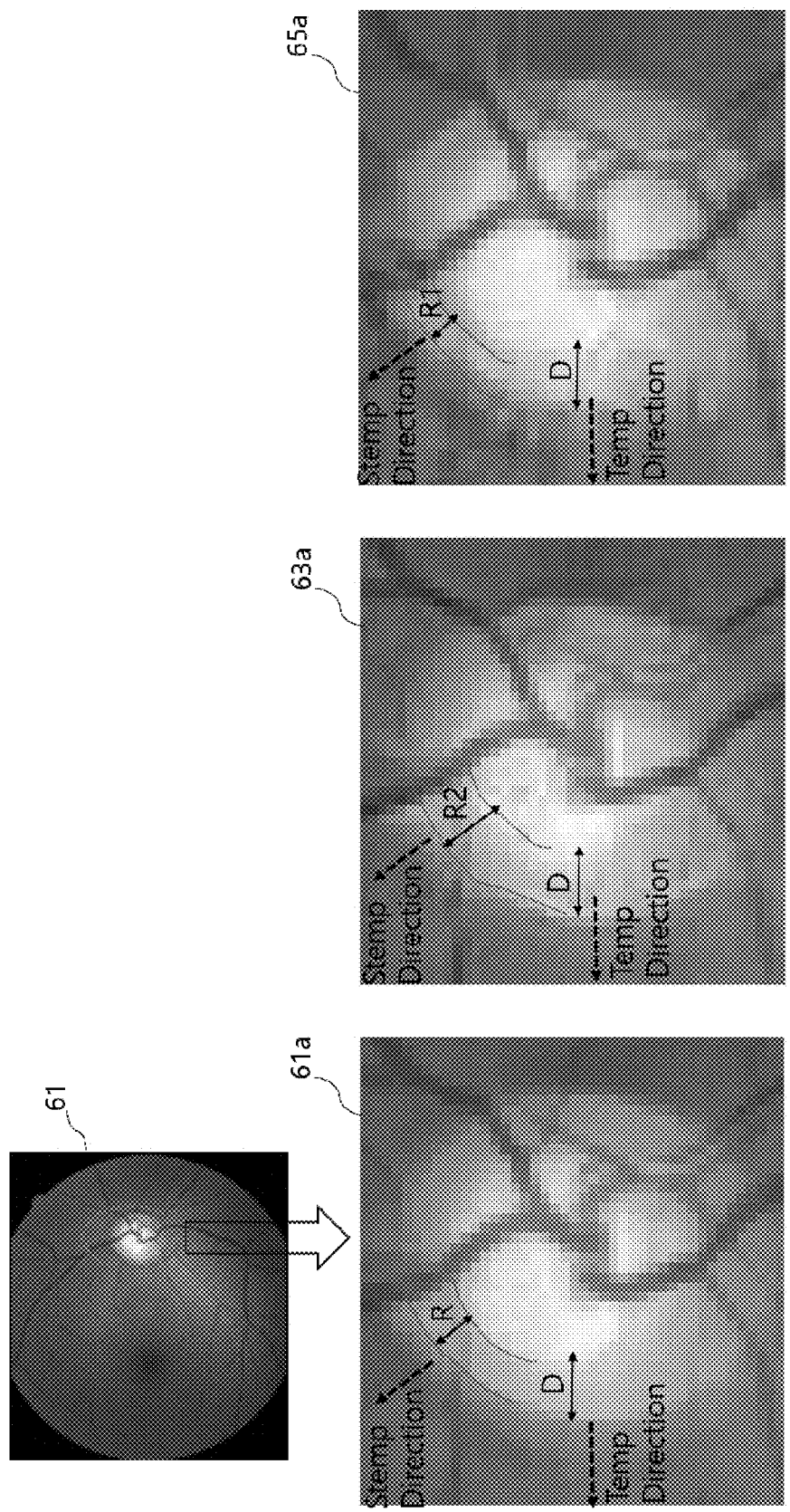
FIG. 6 is a view showing fundus images including a Disc Rim Thinning information acquired by an apparatus according to embodiments of the present disclosure.

FIG. 6 is a view showing fundus images including a Disc Rim Thinning information acquired by an apparatus 100 according to embodiments of the present disclosure. The Rim is defined as an area excluding the area corresponding to the Cup in the Disc area of the fundus image and the Disc Rim Thinning is defined as the degree to which the thickness of the Rim changes in at least one of the Superiotemporal (or Stemp), Superior, Inferiotempal, and Inferior directions defined in the fundus image. Typically, when reading the fundus image, if at least one of the values of the thickness of the Rim in the Superiotemporal, Stemp, Superior, Inferiotempal, and Inferior directions divided by the thickness of the Rim in a Temporal (or Temp) direction is approximately 1.6 or less, or is less than 0.1 times the maximum length of the Disc, the entity has the finding in which there is a disease such as glaucoma in the fundus image.

As depicted, a first fundus image 61 is obtained from the subject based on the machine learning model 13 in FIG. 1, and an enlarged first image 61*a* is obtained by enlarging a disc area in the first fundus image 61. An enlarged second image 63*a* is obtained by enlarging the disc area in a second fundus image (not shown) which is obtained by mapping a negative adversarial factor to the cup and disc area in the first fundus image 61, the enlarged second image 63*a* is an image with the value of the Disc Rim Thinning in the normal range that cannot diagnose any disease based on the machine learning model. An enlarged third image 65*a* is obtained by enlarging the disc area in a third fundus image (not shown) which is obtained by mapping a positive adversarial factor for the cup and disc in the first fundus image 61, the enlarged third image 65*a* is an image with the value of the Disc Rim Thinning in the abnormal range that can diagnose any disease based on the machine learning model. In this case, the first feature information of the first fundus image 61 shows the value of the Disc Rim Thinning, and the second feature information of the second fundus image and the third feature information of the third fundus image show the value of the Disc Rim Thinning changed by mapping the adversarial factor to the first fundus image 61. Thus, the first, second and third feature information may be reflected in the first, second, and third fundus images, respectively. The method of mapping the adversarial factor is similar to mapping described in FIG. 1.

More specifically, the first fundus image 61 obtained based on the machine learning model 13 is a fundus image that can show the findings in which there is a disease such as glaucoma because the value of the Disc Rim Thinning is about 0.56. However, the accuracy or reliability of such findings on the first fundus image 61 may be poor. In embodiments, the processor 111 may generate the second fundus image so that the value of the Disc Rim Thinning is close to the normal range of the fundus image like the enlarged second image 63*a*, or the third fundus image so that the value of the Disc Rim Thinning is close to the abnormal range of the fundus image like the enlarged third image 65*a*. The second and third fundus images may be displayed to the display device 130 so that the entity can compare the first fundus image 61 with the second and third fundus images. Thus, the apparatus 100 can increase the reliability and accuracy of a reading (e.g., a finding, a prediction, a diagnosis) on the first fundus image 61, and can explain the reason for the reading result, since the apparatus 100 can allow the entity to compare the first fundus image 61 with the second fundus image or the third fundus image when reading the fundus image. Also, in embodiments, the apparatus 100 may visualize the adversarial noise of the fundus images so that the entity knows the feature information in which the Disc Rim Thinning is changing at a certain position in the fundus image.

Figure 7:
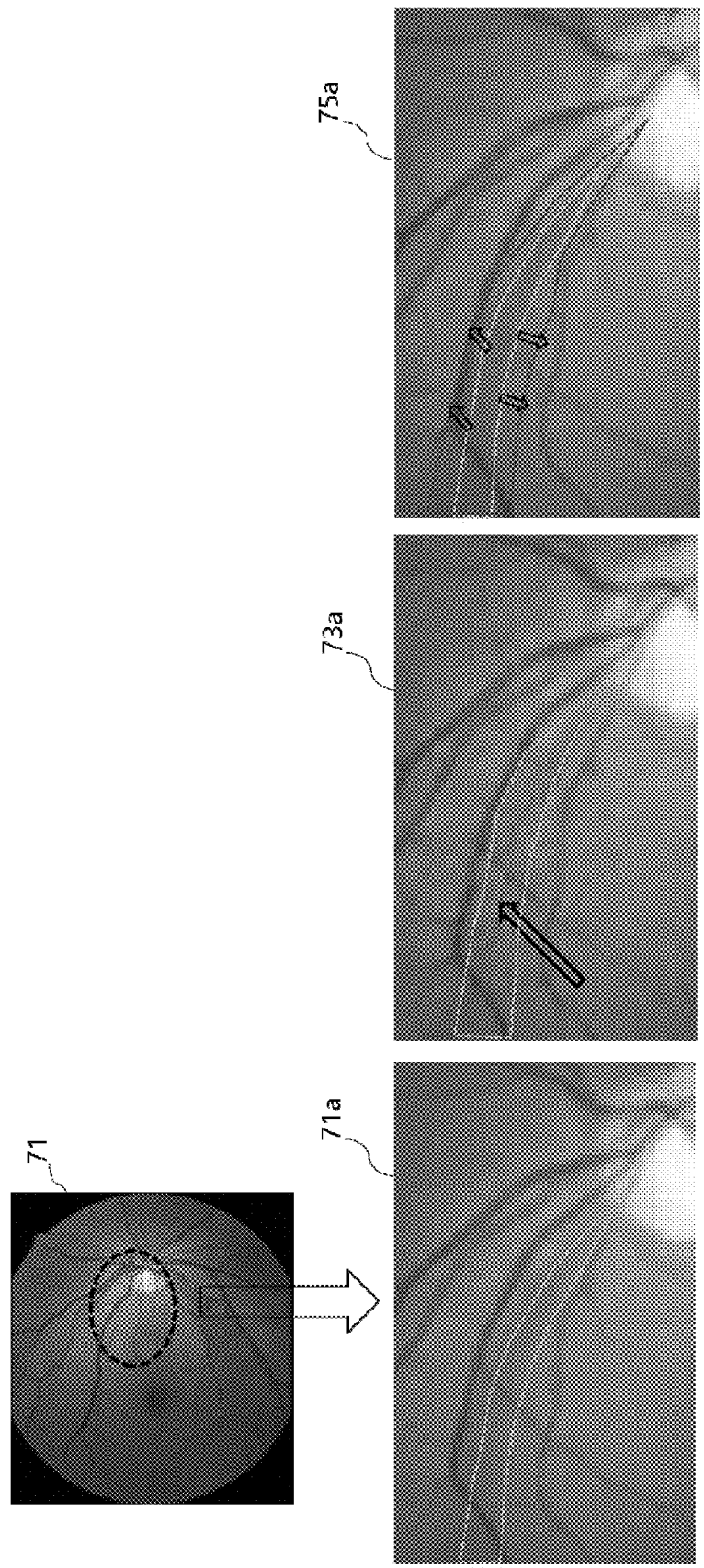
FIG. 7 is a view showing fundus images including a contrast information of a Retinal Nerve Fiber Layer Defect acquired by an apparatus according to embodiments of the present disclosure.

FIG. 7 is a view showing fundus images including a contrast information of a Retinal Nerve Fiber Layer Defect acquired by an apparatus 100 according to embodiments of the present disclosure. Typically, the Retinal Nerve Fiber Layer (hereinafter, RNFL) appears in a fan shape from the disc along a blood vessel in the fundus image, the RNFL Defect means that the RNFL become defective or disappeared in the fundus image. When reading the fundus image, if an area of the RNFL appears dark on the fundus image and a bright pattern of the RNFL is lost, the entity has the finding in which there is a disease such as glaucoma in the fundus image.

As depicted, a first fundus image 71 is obtained from the subject by the apparatus 100 based on the machine learning model 13, and an enlarged first image 71*a* is obtained by enlarging an area where the RNFL appears in the first fundus image 71. An enlarged second image 73*a* is obtained by enlarging the RNFL area in a second fundus image (not shown) which is obtained by mapping a negative adversarial factor for the RNFL in the first fundus image 71, the enlarged second image 73*a* is an image with the contrast of the RNFL in the normal range that cannot diagnose any disease based on the machine learning model. An enlarged third image 75*a* is obtained by enlarging the RNFL area in a third fundus image (not shown) which is obtained by mapping a positive adversarial factor for the RNFL in the first fundus image 71, the third fundus image is an image with the contrast of the RNFL in the abnormal range that can diagnose any disease based on the machine learning model. In this case, the first feature information of the first fundus image 71 shows the contrast information of the RNFL, and the second feature information of the second fundus image and the third feature information of the third fundus image show the contrast of the RNFL changed by mapping the adversarial factor to the first fundus image 71. The method of mapping the adversarial factor may be similar to mapping described in FIG. 1.

More specifically, the enlarged first image 71a obtained based on the machine learning model 13 is a fundus image that can show the findings in which there is a disease such as glaucoma because the RNFL does not appear in a dotted area of the enlarged first fundus image 71a. In embodiments, the processor 111 may generate the enlarged second image 73a by appearing the RNFL in the dotted area so that the enlarged second image 73a is close to the normal range as indicated by the arrow, or the third enlarged image 75a by expanding the dotted area where the RNFL does not appear so that the enlarged third image 75a is close to the abnormal range. The enlarged second and third images 73a, 75a may be displayed on the display device 130 so that the entity can compare the enlarged first image 71a with the enlarged second and third images 73a, 75a. Also, in embodiments, the apparatus 100 may visualize the adversarial noise of the fundus images so that the entity knows the feature information in which the RNFL is changing at a certain position in the fundus image.

Figure 8:
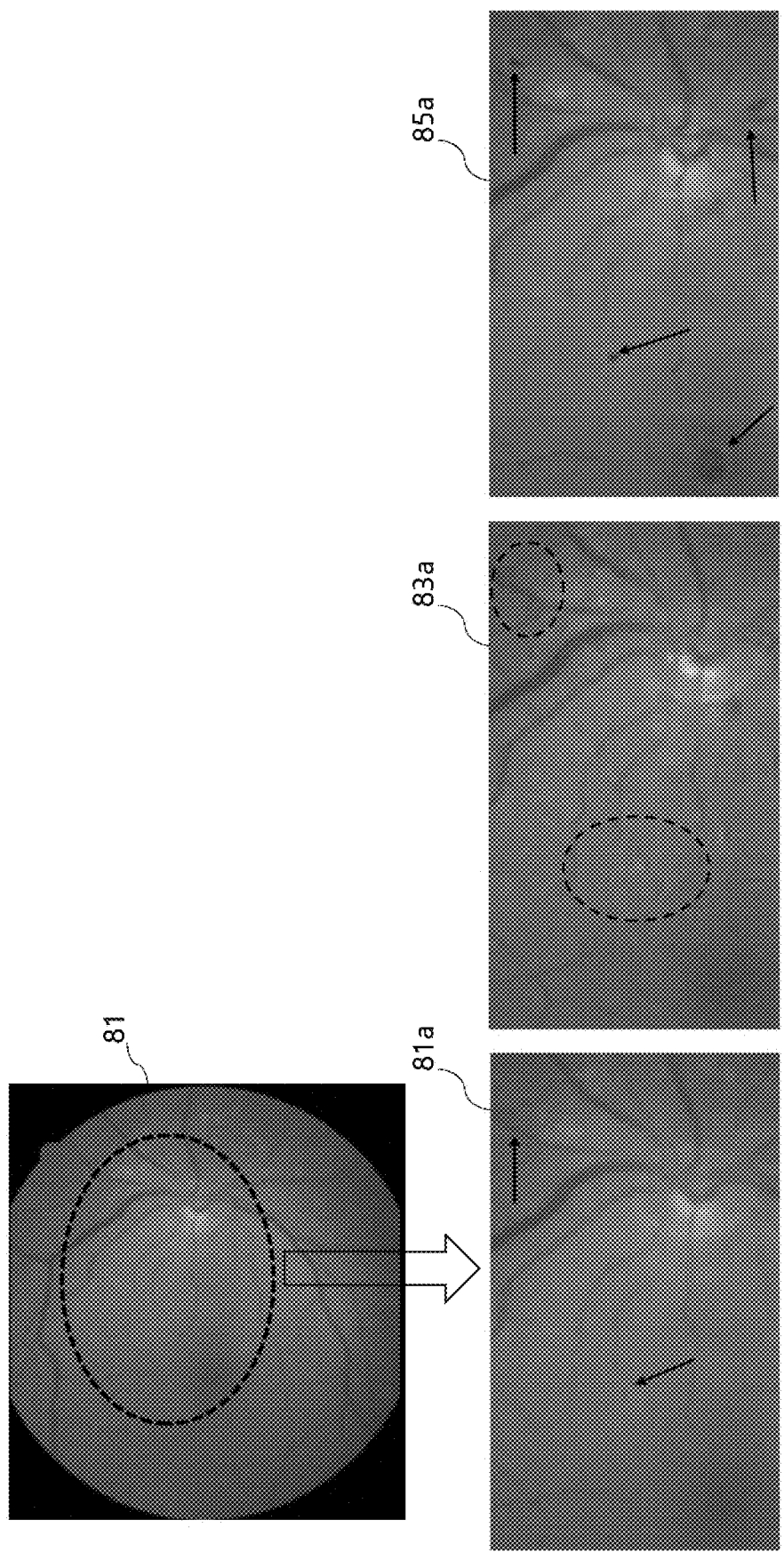
FIG. 8 is a view showing fundus images including a location information of a Retinal Hemorrhage acquired by an apparatus according to embodiments of the present disclosure.

FIG. 8 is a view showing fundus images including a location information of a Retinal Hemorrhage acquired by an apparatus 100 according to embodiments of the present disclosure. Typically, the Retinal Hemorrhage appears as dark or red spots in a specific part of the fundus image caused by rupture of blood vessels distributed in the retina. When reading the fundus image, if the Retinal Hemorrhage appears on the fundus image, the entity has the finding in which there is a disease such as visual impairment in the fundus image.

As depicted, a first fundus image 81 is obtained from the subject by the apparatus 100 based on the machine learning model 13, and an enlarged first image 81a is obtained by enlarging an area where the retinal hemorrhage appeared in the first fundus image 81. An enlarged second image 83a is obtained by enlarging the area where the retinal hemorrhage appeared in a second fundus image (not shown) which is obtained by mapping a negative adversarial factor in the first fundus image 81, the enlarged second image 83a is an image that cannot diagnose any disease based on the machine learning model. An enlarged third image 85a is obtained by enlarging the area where the retinal hemorrhage appeared in a third fundus image (not shown) which is obtained by mapping a positive adversarial factor in the first fundus image 81, the third fundus image is an image that can diagnose any disease based on the machine learning model. In this case, the first feature information of the first fundus image 81 is the location of the Retinal Hemorrhage, and the second feature information of the second fundus image and the third feature information of the third fundus image are the location of the Retinal Hemorrhage changed by mapping the adversarial factor to the first fundus image 81. The method of mapping the adversarial factor is similar to mapping described in FIG. 1.

More specifically, the enlarged first image 81a obtained based on the machine learning model 13 is a fundus image that can show the findings in which there is a disease such as glaucoma because the Retinal Hemorrhage appears on the enlarged first fundus image 71a as indicated by the arrow. In embodiments, the processor 111 may generate the enlarged second image 83a by disappearing the Retinal Hemorrhage in the dotted area so that the enlarged second image 83a is close to the normal range, or the third enlarged image 85a by appearing the Retinal Hemorrhage as indicated by the arrow so that the enlarged third image 85a is close to the abnormal range. The enlarged second and third images 83a, 85a may be displayed on the display device 130 so that the entity can compare the enlarged first image 81a with the enlarged second and third images 83a, 85a. Also, in embodiments, the apparatus 100 may visualize the adversarial noise of the fundus images so that the entity knows the feature information in which the Retinal Hemorrhage is changing at a certain position in the fundus image.

In embodiments, the apparatus 100 may read the fundus image including at least one of a location of Drusen, a Retinal Pigment Epithelium Change, a Chorioretinal Scar/Atrophy, a Peripapillary Atrophy, a Hard Exudate, a Cotton-Wool Patch, a Hemorrhage, a Vascular Abnormality, a Laser Scar, a Subretinal Fluid, a Myelinated Nerve Fiber, and a Epiretinal Membrane, in the reading method described above.

Figure 9A:
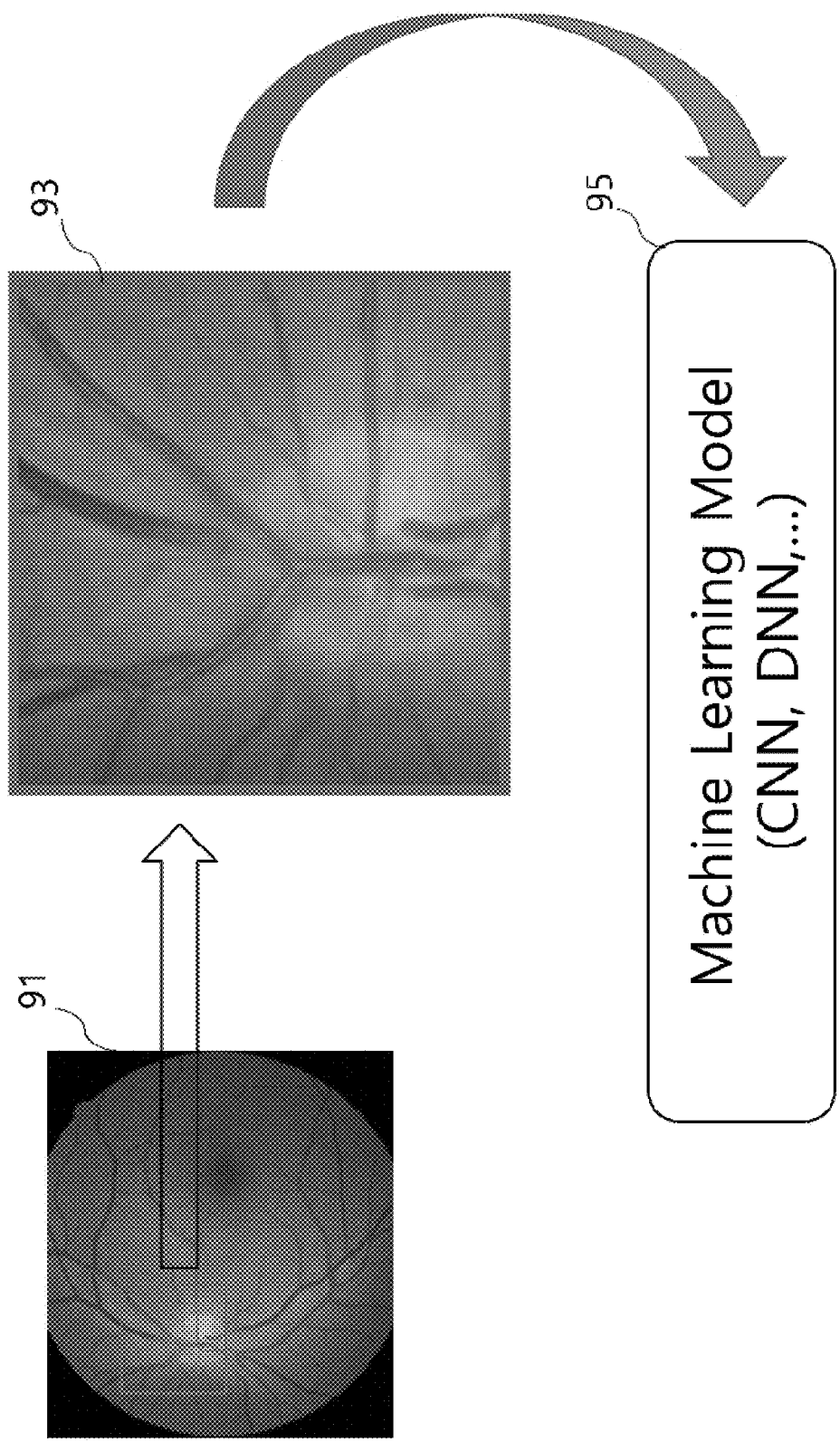
FIGS. 9A and 9B are a view showing an illustrative process for generating a pre-fundus image by apparatus according to embodiments of the present disclosure.
Figure 9B:
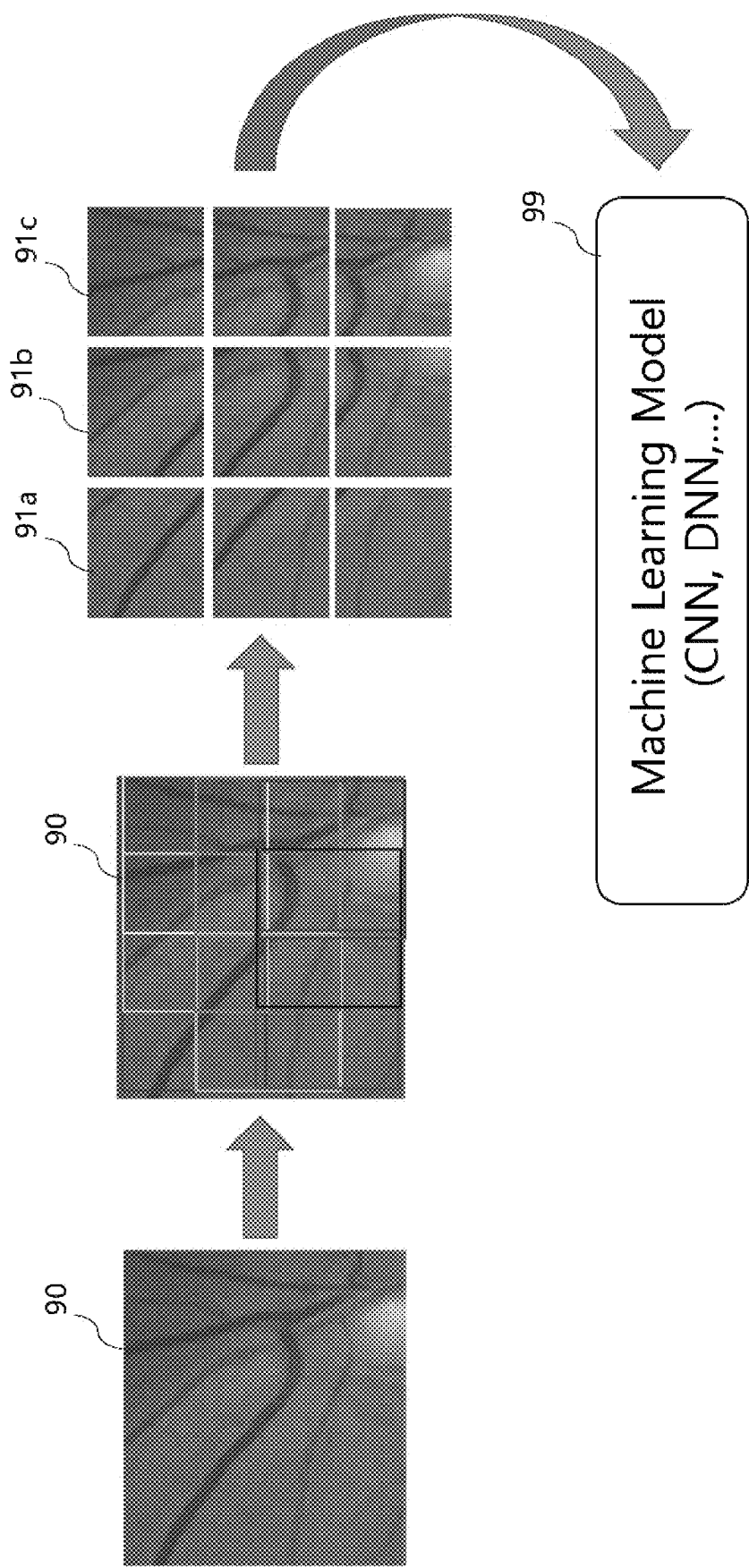

FIGS. 9A and 9B are a view showing an illustrative process for generating a pre-fundus image by apparatus 100 according to embodiments of the present disclosure.

As depicted in FIG. 9A, in embodiments, initially an original fundus image 91 of the subject may be obtained by taking an image by a camera (not shown). After that, pre-fundus image 93 may be generated by pre-processing the original fundus image 91 by the processor 111 in FIG. 1 so that a specific region of the original fundus image is enlarged in order to more intensively check a feature information on the original fundus image 91. In this case, the specific region may be, but is not limited to, the optic nerve papilla region including retinal blood vessels. Finally, The pre-fundus image 93 may be input to the machine learning model 95, and the fundus disease may be predicted by extracting the feature information from the pre-fundus image 93 based on the machine learning model 95.

As depicted in FIG. 9B, in embodiments, First, an enlarged fundus image 90 may be obtained by pre-processing an image like the original fundus image 91 described in FIG. 9A. The pre-processing may be executed by the processor 111 in FIG. 1. After that, the enlarged fundus image 90 may be partially partitioned by a plurality of areas. In this case, each of the plurality of areas may have the same size or different sizes. Each of the plurality of areas may overlap each other locally. At that, a plurality of pre-fundus images 91a, 91b, 91c may be generated according to the partitioned areas. Finally, each of the plurality of pre-fundus images 91a, 91b, 91c may be input to the machine learning model 99 and the fundus disease may be predicted by extracting the feature information from each of the pre-fundus images 91a, 91b, 91c based on the machine learning model 99.

The pre-fundus image may be generated in various ways. For example, the pre-fundus image may be generated by rotating around a reference axis of the original fundus image, or/and the pre-fundus image may be generated by adjusting the contrast or brightness of the original fundus image or/and by flipping around a horizontal or vertical axis of the original fundus image.

Thus, if the pre-fundus image inputs the machine learning model, thereby more improving an accuracy of prediction of the fundus disease.

Figure 10:
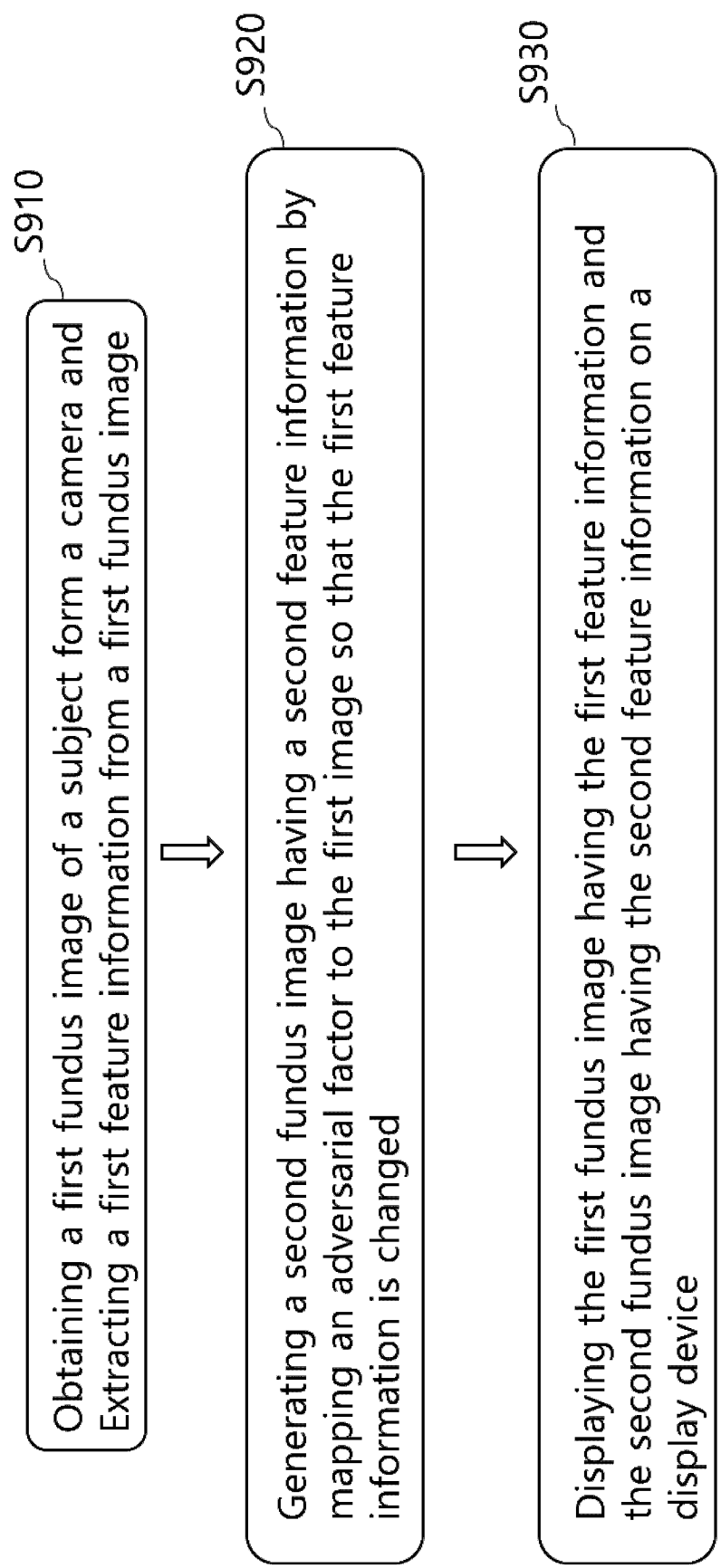
FIG. 10 shows a flowchart illustrating an exemplary process for supporting reading of a fundus image by a processor according to embodiments of the present disclosure.

FIG. 10 shows a flowchart illustrating an exemplary process for supporting reading of a fundus image by a processor 111 according to embodiments of the present disclosure.

At step S910, the processor 111 may obtain a first fundus image of a subject from a fundus camera and extract a first feature information from the first fundus image of the subject. In embodiments, the first fundus image may be stored in the memory unit 113, 313 or the storage device 115, 315 included to the computing device 110, 310 (as discussed in conjunction with FIGS. 2 and 3). At step S920, the processor 111 may map an adversarial factor (i.e., the adversarial noise) to the first fundus image to change the first feature information of the first fundus image, thereby generating a second fundus image with a second feature information. Mapping the adversarial factor may be similar to mapping described in FIG. 1. In embodiments, the processor 111 may generate images in which a specific area of the first fundus image and the second fundus image is enlarged. In embodiments, the processor 111 may generate a third fundus image in which an adversarial noise is visualized, by filtering the second fundus image using an image filter. In alternative embodiments, the processor 111 may generate a pre-first fundus image by pre-processing the first fundus image so that a specific area of the first fundus image is enlarged or partially partitioned. At step S930, the processor 111 may display the fundus image having the first feature information and the second fundus image having the second feature information on a display device so as to provide an entity with the first and second feature information. In embodiments, the processor 111 may display at least one of the enlarged images and the visualized third fundus image on the display device.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present disclosure may further relate to computer products with a non-transitory, tangible computer-readable medium that have computer code thereon for performing various computer-implemented operations. The media and computer code may be those specially designed and constructed for the purposes of the present disclosure, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present disclosure may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present disclosure. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. An apparatus for supporting reading of a fundus image of a subject, comprising:
   a processor; and
   a memory comprising one or more sequences of instructions which, when executed by the processor, causes steps to be performed comprising:
   extracting a first feature information from a first fundus image of the subject based on a machine learning model;
   generating a second fundus image having a second feature information by mapping an adversarial factor to the first fundus image so that the first feature information of the first fundus image is changed;
   generating a third fundus image in which an adversarial noise is visualized, by filtering the second fundus image mapped by the adversarial factor therein; and
   displaying the first fundus image having the first feature information, the second fundus image having the second feature information and the third fundus on a display device.

2. The apparatus of claim 1, wherein the steps further comprises:
   generating images in which a specific area of each of the first fundus image and the second fundus image is enlarged; and
   displaying the images on the display device.

3. The apparatus of claim 1, wherein the steps further comprises:
   generating a pre-first fundus image by pre-processing the first fundus image so as to enlarge or partially partition a specific area of the first fundus image.

4. The apparatus of claim 1,
   wherein the adversarial factor comprises at least one of gradation levels of R, G, and B pixels of the first fundus image, a color of R, G, and B pixels of the first fundus image, and a contrast ratio of the first fundus image.

5. The apparatus of claim 1,
   wherein the second fundus image is generated by repeatedly mapping by the adversarial factor to the first fundus image at least one or more times so that a prediction value of the first feature information obtained based on the machine learning model for the first fundus image converges to a set value.

6. The apparatus of claim 5,
   wherein the number of second fundus image is dependent on the number of a set value.

7. The apparatus of claim 1,
wherein the first feature information is extracted by utilizing a clinical information of the subject.

8. The apparatus of claim 1,
wherein the first feature information comprises at least one of a cup-to-disk ratio, a thickness change for a disc rim thinning, a contrast for a retinal nerve fiber layer defect and, a location of a retinal hemorrhage included in the first fundus image.

9. A non-transitory computer-readable medium or media comprising one or more sequences of instructions which, when executed by a processor, causes steps for supporting reading of a fundus image of a subject, comprising:

extracting a first feature information from a first fundus image of the subject based on a machine learning model;

generating a second fundus image having a second feature information by mapping an adversarial factor to the first fundus image so that the first feature information of the first fundus image is changed;

generating a third fundus image in which an adversarial noise is visualized, by filtering the second fundus image mapped by the adversarial factor therein; and displaying the first fundus image having the first feature information, the second fundus image having the second feature information and the third fundus on a display device.

10. The non-transitory computer-readable medium or media of claim 9, wherein the steps further comprises:

generating images in which a specific area of each of the first fundus image and the second fundus image is enlarged; and displaying the images on the display device.

11. The non-transitory computer-readable medium or media of claim 9, wherein the steps further comprises:

generating a pre-first fundus image by pre-processing the first fundus image so that a specific area of the first fundus image is enlarged or partially partitioned.

12. A method for supporting reading of a fundus image of a subject, comprising:

extracting a first feature information from a first fundus image of the subject based on a machine learning model;

generating a second fundus image having a second feature information by mapping an adversarial factor to the first fundus image so that the first feature information of the first fundus image is changed;

generating a third fundus image in which an adversarial noise is visualized, by filtering the second fundus image mapped by the adversarial factor therein; and displaying the first fundus image having the first feature information, the second fundus image having the second feature information and the third fundus on a display device.

13. The method of claim 12, further comprising:

generating images in which a specific area of each of the first fundus image and the second fundus image is enlarged; and displaying the images on the display device.

14. The method of claim 12, further comprising:

generating a pre-first fundus image by pre-processing the first fundus image so that a specific area of the first fundus image is enlarged or partially partitioned.

15. The method of claim 12,
wherein the adversarial factor comprises at least one of gradation levels of R, G, and B pixels representing the first fundus image, a color change of R, G, and B pixels, and a contrast ratio in the first fundus image.

16. The method of claim 12,
wherein the second fundus image is generated by repeatedly mapping the adversarial factor at least one or more times so that a prediction value of the second feature information obtained based on the machine learning model for the first fundus image converges to a set value.

17. The method of claim 12,
wherein the first feature information comprises at least one of a cup-to-disk ratio, a thickness change for a disc rim thinning, a contrast for a retinal nerve fiber layer defect and, a location of a retinal hemorrhage included in the first fundus image.

* * * * *